United States Patent [19]

Balding et al.

[11] 4,170,421
[45] Oct. 9, 1979

[54] RECIPROCAL STERILIZING AGITATOR SYSTEM (RSAS)

[75] Inventors: David P. Balding, El Toro; Victor V. Menayan, Lake Forest, both of Calif.

[73] Assignee: American Hospital Supply Corporation, Evanston, Ill.

[21] Appl. No.: 939,627

[22] Filed: Sep. 5, 1978

[51] Int. Cl.² .............................................. B01F 15/06
[52] U.S. Cl. ...................................... 366/144; 99/348; 99/483; 422/297; 426/521
[58] Field of Search ............... 366/144, 145, 146, 147, 366/149, 148, 203, 212, 240; 99/348, 483, 467, 468, 485; 426/521, 522; 422/297, 300

[56] References Cited

U.S. PATENT DOCUMENTS

| | | | |
|---|---|---|---|
| 1,409,286 | 3/1922 | Diner | 422/297 |
| 2,734,826 | 2/1956 | Stentz | 426/522 |
| 3,635,150 | 1/1972 | Piedallu | 366/240 |
| 3,721,527 | 3/1973 | Lodige | 426/521 |
| 3,994,684 | 11/1976 | Tomasulo | 422/297 |
| 4,059,919 | 11/1977 | Green | 426/521 |

*Primary Examiner*—Robert W. Jenkins

[57] ABSTRACT

The invention provides an agitator system primarily for use in the production of liquids and semi-liquids which may be agitated during a sterilization process. A sealed chamber may be filled with live steam or a mixture of steam and air or water. Inside the chamber is a relatively simple table mount which enables a reciprocal motion of a product continuously during the entire or a part of the process. A suitable driving power source is positioned outside of the chamber and connected through the chamber wall to give a reciprocal motion to the table. The driving power source is adapted to accommodate any of a plurality of production variables such as changes in: length of stroke or amplitude of vibration, rate of stroke or frequency of vibration, rate of acceleration or deceleration, or the like.

9 Claims, 5 Drawing Figures

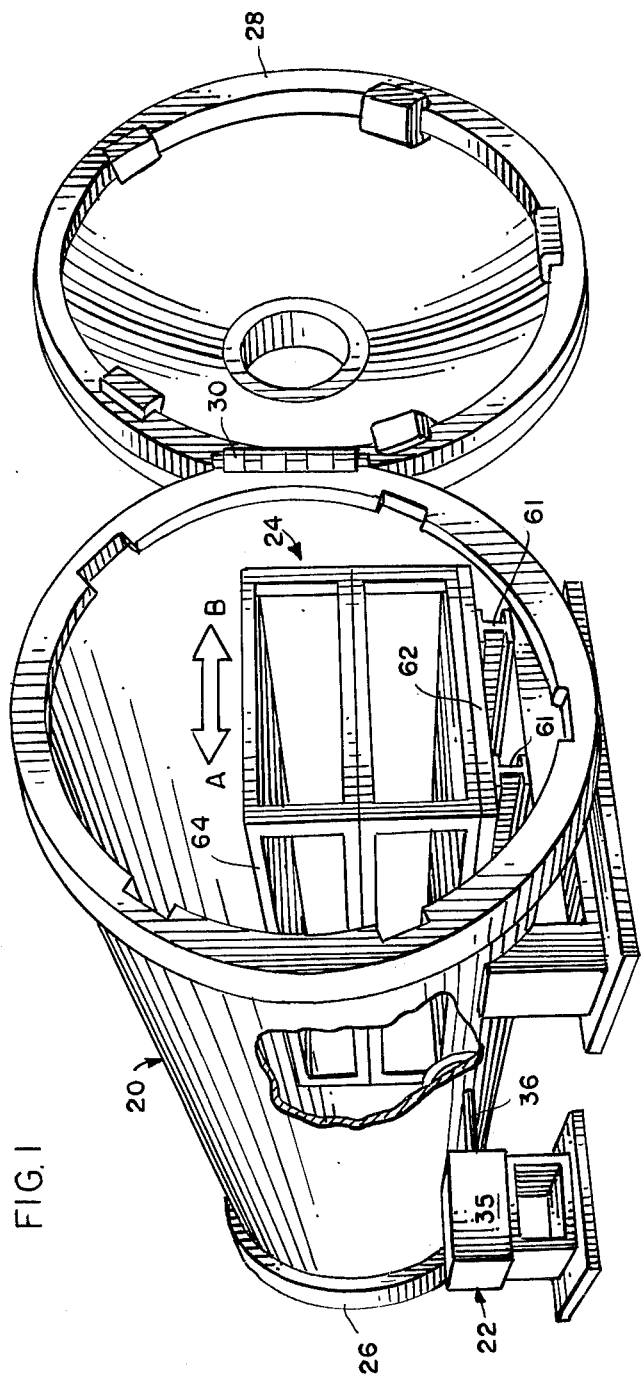
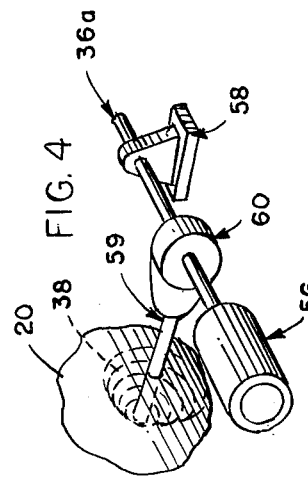
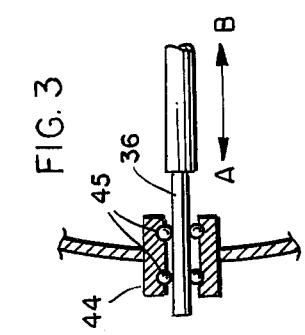
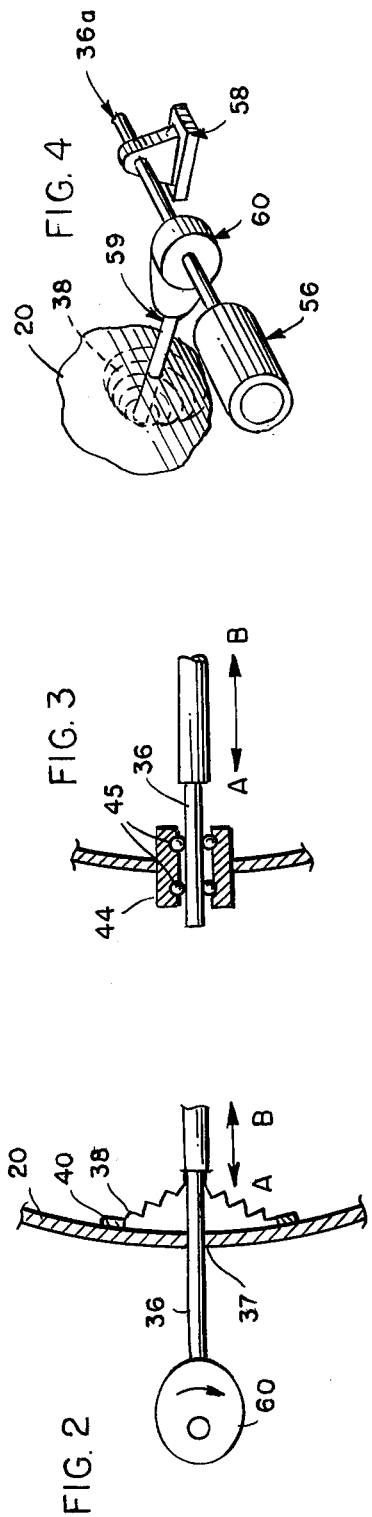

RECIPROCAL STERILIZING AGITATOR SYSTEM (RSAS)

This invention relates to sterilizer systems and more particularly to sterilizer systems with reciprocal linear agitators.

There are many times for, places of and reasons why a substance must be agitated in a sterilizer environment. Two examples of industries which may use such devices are the food processing industry and the pharmaceutical or hospital supply industry. In each of these and similar industries there is a product which can be agitated during sterilization.

Heretofore, there has generally been a rotary fixture for holding the product containers while the containers either rotated in an axial position or rotated end over end. Either way, the product is tumbled. Substantial supports are required for supporting a fairly large and rotating fixture. Also, substantial amounts of time are required for loading and unloading the sterilizer vessel with the rotary fixtures and the product. Other considerations relate to degradation of a product during sterilization and uniformity of the sterilization temperature distribution through the product, simplification of production and ease of maintenance. Still other factors to be considered relate to conservation of energy, cost of production and the like.

Accordingly, an object of this invention is to provide new and improved means for and methods of processing products which can be agitated continuously or during a portion of the sterilization process. Here an object is to simplify sterilization procedures and to reduce the number and complexity of moving parts within a sterilizer. This is important since the environment inside a sterilizer is a harsh one.

Yet another object of the invention is to enable more accurate monitoring of the process and the products during sterilization. In this connection probes, sensors and the like are placed in or connected to products or their containers and wired directly from the products or containers to recording and control instruments.

Still another object is to provide a controllable amount of agitation within an easily accessible sterilization chamber.

In keeping with an aspect of the invention, these and other objects are accomplished by providing a sealed chamber which may be filled with live steam or mixtures of steam and air or water. The only parts within the chamber are relatively simple device which enable a reciprocal motion of a table. A suitable driving power source is positioned outside of the chamber and connected through the chamber wall to give a reciprocal motion to the table inside the chamber. The driving power source is adapted to accommodate variables in a production process such as changes in: length of stroke or amplitude of vibration, rate of stroke or frequency of vibration, acceleration of deceleration, or the like. Hence, except for the seal at a point where the driving power is transmitted through the chamber wall and for the reciprocal mount, virtually no production equipment is exposed to the harsh sterilizing environment within the chamber.

Two embodiments for accomplishing the foregoing and other objects are shown in the attached drawings, wherein:

FIG. 1 is a perspective, partly cutaway view of a first embodiment of a reciprocal sterilizer agitator system incorporating a side drive, a spring table mount and a double-door chamber;

FIG. 2 shows a fragment of a chamber wall, bellows seal between the driving power source and the reciprocal table;

FIG. 3 shows a fragment of a chamber wall, linear bearing and drive shaft;

FIG. 4 shows a fragment of a chamber wall rotary bearing and crank arm drive shaft.

Figure 5:
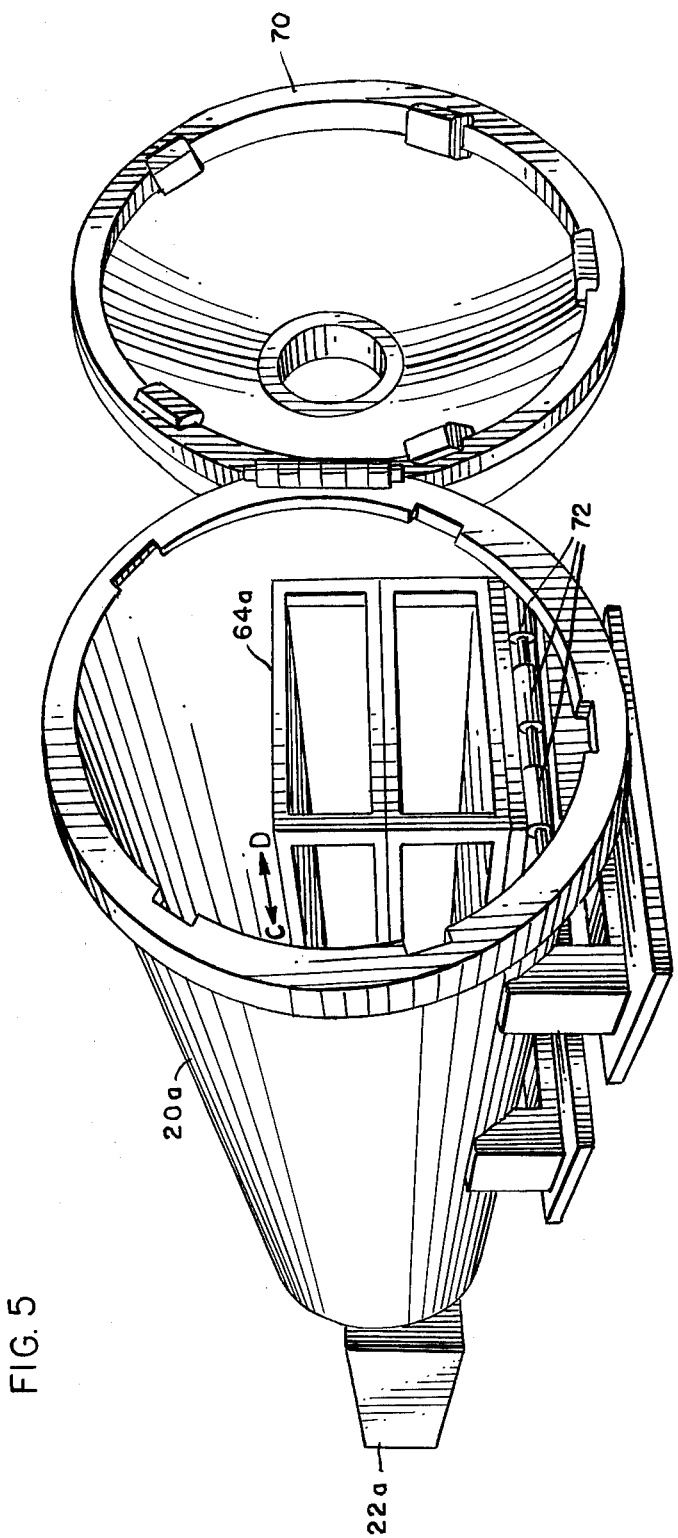
FIG. 5 shows, in perspective, a second embodiment of a reciprocal sterilizer agitator system featuring a rear drive, a roller-mounted table and a single door chamber.

The embodiment of FIG. 1 has three principal subsystems which are a generally cylindrical and pressurized sterilization chamber 20, a power drive source 22 and a product support means, preferably in the form of a reciprocal table mount 24. In this embodiment, both of the ends of the cylindrical chamber are unencumbered so that there may be a door 26,28 on each end, if desired.

The power drive source 22 may include any suitable device such as a pneumatic or hydraulic actuator or an electrical motor for driving a suitable mechanical cam or mechanically eccentric device for providing a reciprocal motion inside of the chamber 20.

The drive shaft 36 of such power drive may pass through any suitable seal in the chamber wall. For example, FIG. 2 shows shaft 36 sealed to a chamber wall opening 37 through a bellows or diaphragm 38 which is also sealed at its periphery 40 to the wall of chamber 20. The bellows, or diaphragm 38, has a sufficient flexibility to enable a desired amount of reciprocal shaft motion in directions A,B. FIG. 3 shows the shaft 36 as sliding in directions A,B through a linear bearing 44 sealed in a hole through the wall of chamber 20. Any suitable O-rings, or the equivalent 45, may seal the shaft 36 in the bearing 44. FIG. 4 shows yet another embodiment wherein a rotary shaft 36a outside the chamber 20 is connected to an eccentric bearing 50 suitably supported at its distant end in a bearing 58. The eccentric bearing 50 is selected to provide a reciprocal linear motion A,B to arm 59 responsive to the circular motion generated by the motor 56.

Each of these power-transmitting systems may include any suitable means for adjusting the length of the reciprocal stroke. For example, a series of replaceable mechanical cams 60 (FIG. 2) may have profiles cut for imparting any suitable reciprocal motions of different amplitudes acceleration and deceleration to the arm 36 or the pneumatic or hydraulic actuators can be selected to provide adjustable stroke lengths.

Inside the chamber 20, there is a reciprocal table mount 24, which comprises pairs of vertically-oriented leaf springs 61,61 in their vertical dimension, the table is capable of undertaking a transverse reciprocal motion in the directions A,B, which is along a diameter of the cross section of chamber 20, responsive to power transmitted from source 22 through the chamber 20 walls to the table top 22. This power may be transmitted in any of the ways disclosed by FIGS. 2-4 or equivalents thereof.

Mounted on the top of the table 62 is any suitable product support or handling means. As here shown, by way of example, a rack of shelves 64 is anchored to the top of table 62. Thus, when the chamber door 28 is opened, the products to be processed are slid onto the shelves 64. Or, alternatively, the shelves 64 may be loaded or unloaded outside of the chamber and then the shelves themselves may be slid onto or off of the table top. The products may be fed into the chamber 20, through the door 28 and removed through the door 26 on the other end of the chamber. Of course, products supports other than the rack of shelves 64 may also be provided, as desired.

FIG. 5 shows a second embodiment wherein the chamber 20a has only a front door 70. The power source 22a is positioned at the back of the chamber 20a to transmit reciprocal forces in the directions C,D which are parallel to the long axis of the chamber. Inside the chamber 20a a number of rollers (such as 72) are positioned to receive and support the products which are fed into the chamber. Here, the rack of shelves 64a is shown as being supported by the rollers 72. This rack 64 may be pulled out of the chamber, loaded or unloaded and then pushed back into the chamber. During sterilization, the rack may be reciprocally rocked back and forth on the rollers.

Other product-holding systems may include pallets, trays, or the like.

The advantages of the invention should now be clear. The invention is primarily directed to provide agitation during the sterilization of liquid or semi-liquid products, but it may also be used with any other products which must be agitated inside a closed container. The invention lends itself to use with any kind of control system: electronic, electrical, pneumatic or mechanical. Therefore, it may be used in any system ranging from sophisticated computer-controlled to the simplest manually-controlled production systems. Any of these systems may use any known techniques for adjusting the amplitude, frequency, acceleration or deceleration of the vibrations. There are significant reductions in cost and maintenance as compared to other systems.

In addition to the aforementioned reductions in cost and maintenance, a significant reduction in sterilization time is also observed. As noted from Chart 1 below with an increase of 8° C. and agitation, a 25-33% decrease in sterilization time is obtained.

motion transmitted from said driving power source to said product support means.

3. The agitator system of claim 1 wherein said product support means comprises vertically-oriented leaf springs extending longitudinally through said chamber, the lower edges of said leaf springs being anchored to the inside bottom of said chamber, and table means attached to the upper edges of said leaf springs, whereby said table moves reciprocally responsive to a flexing of said springs in their vertical orientation.

4. The agitator system of claim 1 wherein said product support means comprises a plurality of roller means positioned to rotate about parallel axes, and table means resting upon and moving with rotation of said roller means.

5. The agitator system of claim 1 wherein said chamber means is an elongated chamber, and said driving power source means transmits said power through the side of said chamber, said product support means being mounted for reciprocal motion perpendicular to the elongated dimension of said chamber responsive to the power transmitted through the side of said chamber.

6. The agitator system of claim 5 wherein said product support means comprises vertically-oriented leaf springs extending longitudinally through said chamber, the lower edges of said leaf springs being anchored to the inside of said chamber, table means attached to the upper edges of said leaf springs, and means for connecting said driving power source means to said table intermediate the ends thereof to drive said table in a direction perpendicular to the leaf springs whereby said driving power source reciprocally moves the table by flexing said springs in their vertical orientation.

7. The agitator system of claim 1 wherein said chamber is an elongated chamber and said driving power source means transmits said power through an end of said chamber, said power support means comprising a table mounted for vibratory motion along the elongated dimension of said chamber responsive to the power transmitted through the end of said chamber.

| | | Sterilization Cycle Time Reduction[1] | | | | |
|---|---|---|---|---|---|---|
| | 252° F. exposure, static containers | 252° F. exposure RSAS agitated containers | Cycle time reduction | 260° F. exposure, static containers | 260° F. exposure RSAS agitated containers | Cycle time reduction |
| 1000 ml glass container 50% dextrose solution | 58 min. | 50 min. | 8 min −14% | 54 min. | 39 min. | 15 min. −28% |
| 2000 ml plastic container 50% dextrose solution | 80 min. | 70 min. | 10 min. −13% | 66 min. | 60 min. | 6 min. −9% |

[1]Times are for total cycle time, including heating and cooling for an Fo = 10-15.

Those who are skilled in the art will readily perceive how to modify the system. Therefore, the appended claims are to be construed to cover all equivalent structures.

The invention claimed is:

1. A reciprocal sterilizing agitator system comprising chamber means which may be sealed and elevated to sterilizing temperatures with a controlled environment enclosed therein, product support means in said chamber for enabling a reciprocal motion to be imparted to said product, and driving power source means outside of said chamber for transmitting a reciprocal motion through walls of said chamber to said product support means.

2. The agitator system of claim 1 and means for adjusting the amplitude and frequency of the reciprocal 8. A method for processing a product which may be agitated continuously while sealed in a sterilizing environment, said method comprising the steps of:
   a. mounting a table for reciprocal motion in a sealed chamber;
   b. reciprocally moving said table responsive to power transmitted through the wall of said chamber; and
   c. adjusting the amplitude and frequency of said reciprocal motion responsive to said transmitted power.

9. The method of claim 8 and the added step of sealing said chamber at the location where the power is transmitted through the chamber wall in order to protect the source of the power from the sterilizing environment established within the chamber.

* * * * *